United States Patent

Buess et al.

[11] Patent Number: 5,800,451
[45] Date of Patent: Sep. 1, 1998

[54] TROCAR SYSTEM

[75] Inventors: Gerhard Buess, Tübingen; Andreas Melzer, Duisburg; Franz Jakoubek, Liptingen; Joachim Krauter, Korb, all of Germany

[73] Assignee: Willy Rüsch AG, Kernen-Rommelshausen, Germany

[21] Appl. No.: 676,357

[22] PCT Filed: Jan. 16, 1995

[86] PCT No.: PCT/DE95/00058

§ 371 Date: Oct. 25, 1996

§ 102(e) Date: Oct. 25, 1996

[87] PCT Pub. No.: WO95/19146

PCT Pub. Date: Jul. 20, 1995

[30] Foreign Application Priority Data

Jan. 18, 1994 [DE] Germany .................. 44 01 237.3

[51] Int. Cl.⁶ .................................................. A61B 17/34
[52] U.S. Cl. .................................... 606/185; 604/169
[58] Field of Search ............................. 606/185, 167, 606/172; 604/167, 164, 169, 168, 165

[56] References Cited

U.S. PATENT DOCUMENTS 3,717,151  2/1973  Collett .
5,147,316  9/1992  Castillenti .
5,350,393  9/1994  Yoon ....................................... 604/167
5,603,702  2/1997  Smith et al. ........................... 604/167

FOREIGN PATENT DOCUMENTS 0474124  3/1992  European Pat. Off. .
0535974  4/1993  European Pat. Off. .
2218901  10/1973  Germany .
9108043  10/1991  Germany .
9112550  11/1991  Germany .
4129237  3/1993  Germany .
4134655  4/1993  Germany .
4312147  10/1993  Germany .

Primary Examiner—Michael Buiz
Assistant Examiner—Kevin Truong
Attorney, Agent, or Firm—Paul J. Vincent

[57] ABSTRACT

A trocar system (10) comprises a trocar tube (11), a trocar plunger (12) and a valve housing (13) formed on the end of the trocar tube (11) facing away from the patient. The trocar tube (11) is produced from a flexible material which is stabilized by a spiral (22). The trocar tube (11) has a taper at the end (21) next to the patient which can be supported at a circular shoulder (15) with the trocar plunger (12) inserted into the trocar tube (11). The trocar tube (11) can be bent in the direction of arrow (23) and stretched in the direction of arrow (24).

10 Claims, 1 Drawing Sheet

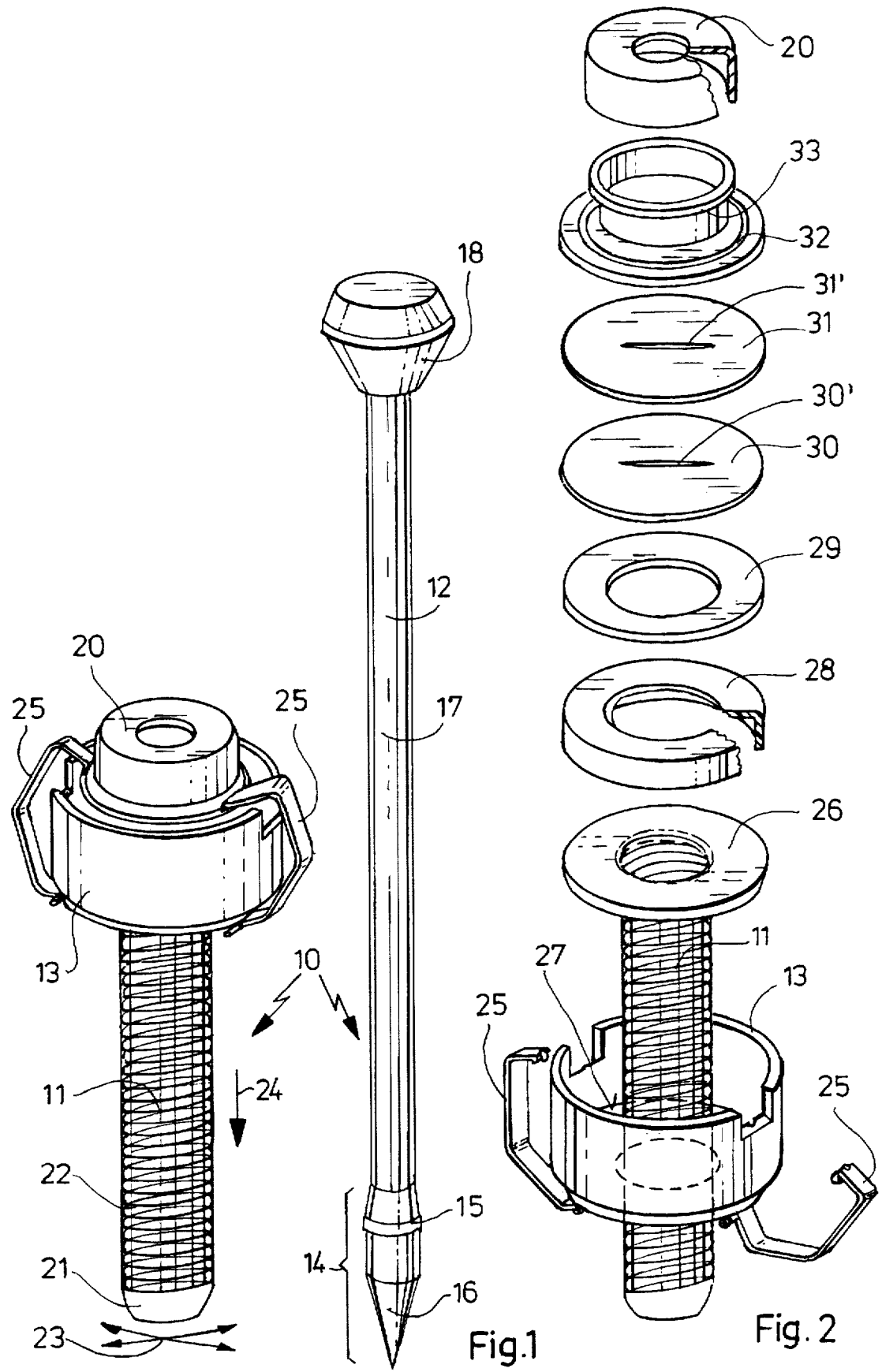

TROCAR SYSTEM

BACKGROUND OF THE INVENTION

The invention concerns a trocar system having a flexible trocar tube defining a lumen, a trocar plunger and a valve mechanism formed at the end of the trocar tube facing away from the patient through the valve housing of which the trocar plunger can be inserted into the trocar tube.

These types of trocar systems are known in the art from DE-OS 43 12 147. These trocar systems comprise an obturator made from rust-free steel or from another rigid material and a cannula made from plastic, such as PTFG, polyurethane or PVC. The cannula made from this type of plastic has an open proximal and open distal end and is flexible to facilitate the introduction of a curved surgical instrument through the cannula into the body cavity without having to increase its inner diameter.

Known in the art from DE-OS 41 34 655 is an atraumatic cannula having a mandrin with an outer cross section and a shaft with an inner cross section which are tapered in the vicinity of the shaft tip such that, when introducing the cannula into the tissue, the pressure on the mandrin facilitates contact between its tapering and the tapering of the shaft to "carry" same and cause stretching thereof while avoiding displacement of its material.

The trocar system in accordance with DE-OS 43 12 147 is fundamentally suitable for the introduction of a curved operation instrument into a hollow body region. However, the operation instrument can cause back and forth motion or displacement of the trocar tube within the tissue. For this reason it is necessary for the trocar tube to be securely anchored in the tissue, in particular, when very strongly curved instruments are introduced.

It is therefore the underlying purpose of the invention to further improve conventional flexible trocar systems in such a fashion that the anchoring of the trocar tube within the tissue is improved and to also guarantee the possible introduction of strongly curved instruments into the trocar tube.

SUMMARY OF THE INVENTION

This purpose is achieved in accordance with the invention in that the trocar tube is stretchable with respect to the axial length and the trocar tube is tapered at the end next to the patient, the taper interlockingly engaging a circular step or a conical section at the tip of the trocar plunger.

The taper is formed in such a fashion that it is capable of close interlocked seating in the tip region of the trocar plunger. In this fashion the tapering engages a circular step or a conical section at the tip of the trocar plunger. The interlocking connection can accept axial forces acting in opposition to the pushing and positioning direction of the trocar tube. A flange is formed at the end of the trocar tube facing away from the patient which can seat in the valve housing. The flange can be strengthened by inlays in the flange material or by support rings and is held within the valve housing in an axially non-displaceable fashion. In further embodiments of the invention, it would also be possible for the trocar tube to be held within the valve housing in a rotatable manner.

A trocar configured in accordance with this technical teaching has the advantage that the trocar tube can be pretensioned at the trocar plunger in a defined fashion. It is therefore possible to prevent an unacceptable excessive stretching of the trocar tube. In the event that the trocar tube is pretensioned it can, for example, be connected in a detachable fashion to the trocar plunger via the valve housing. Towards this end, the trocar tube is supported on the circular step of the trocar plunger and is preferentially attached at the other side to the trocar plunger via the end in proximity to the machine. In the event that the trocar plunger shaft is thinner than its tip, it is possible for the trocar plunger to easily slide within the trocar tube until the tip of the trocar plunger interlocks with the trocar tube taper.

An additional advantage of a trocar configured in accordance with the invention is that the cross section of the trocar tube is reduced when the trocar tube is lengthened. After removal of the trocar plunger from the trocar tube same contracts again and is thereby shortened. In this fashion the cross section of the trocar tube is increased. This increase in cross section increases the strength with which the trocar tube is anchored in the tissue. In this fashion the traumatic effect of the tube within the tissue is reduced and the attachment or anchoring of the trocar tube within the tissue is significantly increased to prevent slipping of the trocar tube during the operation.

The improved anchoring of the trocar tube within the tissue also advantageously prevents gas from unintentionally escaping out of the hollow body region.

The trocar system in accordance with the invention also has the substantial advantage that the trocar tube is guided without compression even in the event that large axially directed forces act on the tip of the trocar tube bushing. During insertion into a tissue layer, the trocar plunger carries the trocar tube along with it without having the trocar tube be displaced in a direction opposite to that of the placement and pushing direction. In the event that the trocar tube and the trocar plunger are adapted to each other in accordance with the invention, it is also possible to position tube shafts having a stiffness of insufficient strength with respect to an axially directed force.

In the event that the trocar tube is manufactured from an elastic pipe-shaped material which is adapted for suitable acceptance of radial forces, it is possible to guarantee the gas-tightness both in the shaft region as well as in the valve region via the rubber elastic sealing ring or rings to successfully prevent the danger of an undesired narrowing of the lumen along the trocar tube. When selecting the shaft material, it is possible to provide for a trocar tube which bends when the trocar plunger is removed to accept even strongly curved instruments while preventing, with unchanged lumen, an unacceptable buckling during introduction of curved instruments.

In a preferred embodiment of the invention, the trocar tube is configured as a spiral jacketed with elastic material whose individual spiral windings are separated from each other, with the elastic material closing the intermediate space between the individual spiral windings along the axial length of the trocar tube.

The spiral can be configured as a spiral wire spring jacketed with an elastic material having good low friction characteristics. The spiral wire reliably prevents the lumen of the trocar tube from unacceptably changing when bent to avoid difficulties when inserting an instrument. The spiral can be configured as a ring at the free end next to the patient which is jacketed, as is the remaining wire insert along the entire length of the trocar tube, with a plastic material to which tissue is insensitive. The wire insert can be of arbitrary construction and must not necessarily be configured as a spiral spring.

In a further configuration of the invention the trocar plunger has a greater axial length than the trocar tube in its non-operative state.

This has the advantage that the trocar tube can be lengthened prior to insertion. If the cross section of the trocar plunger is smaller, with regard to its diameter, than the trocar tube, same can taper in diameter when axially stretched. This facilitates insertion of the trocar plunger into a tissue layer, since the reduced overall cross section likewise results in a reduction in the insertion resistance.

In another preferred embodiment of the invention the valve mechanism is held within the valve housing, same having at least one elastic seal which surrounds the trocar plunger within the trocar tube in a gas-tight fashion to cause a gas-tight sealing of the lumen when the trocar plunger is removed.

In the event that one or a plurality of sealing discs are utilized as a valve mechanism, a reduced axial construction height is possible in the valve region and the sealing region has additional flexibility. Curved or highly curved surgical instruments of an arbitrary kind can be easily passed through the trocar tube with a defined lumen, since the sealing disc or discs do not reduce or block the lumen in the vicinity of the valve mechanism. It is possible for the sealing rings to give-way under pressure and they can be quickly replaced when needed without additional expense.

A further embodiment of the invention comprises a valve housing which can be disassembled.

The trocar tube is held and guided within the valve housing. The flange seats on the housing floor at the inner side of the valve housing. Support rings or sealing discs can be adjacent to the flange. The valve housing is closed via a housing lid which presses the sealing disc or discs against the flange of the tubular shaft. The housing lid can be held to the valve housing using clamps. The valve housing can be easily disassembled and cleaned when the clamps are released. Defective individual components can be quickly replaced. Suitable sealing discs or sealing rings can be utilized as sealing means in the valve housing.

In a further advantageous embodiment of the invention all individual components of the trocar system are made from material which can be cleaned and sterilized.

This has the advantage that the trocar system in accordance with the invention can be utilized a plurality of times. If necessary, the sealing means can be replaced to always guarantee the gas-tight behaviour of the system.

In a further embodiment of the invention, the trocar tube comprises retention means on the outer peripheral surface, preferentially in the vicinity of the end facing away from the patient, such as, for example, tabs, wings, ring-shaped elements, or an inflatable cuff. This has the advantage that the trocar tube in accordance with the invention can, for example, also be secured in the stomach wall of a patient. In the event that the seated trocar tube is displaced in an inappropriate fashion, the retention means oppose this motion. A significant self-fixing of the trocar tube in accordance with the invention is also already achieved by the fact that the extended positioned trocar tube strives to return to its original length when the trocar plunger is removed. In this fashion, the outer diameter of the trocar tube increases and the outer contours of the trocar tube penetrate into the immediately adjacent tissue. In this fashion, the trocar tube is securely held in position.

With the trocar system in accordance with the invention, flexible trocar tubes can be securely supported at the trocar plunger end region from insertion up to final positioning to avoid an unallowed compression of the trocar tube material. A reduced constructional height in the vicinity of the valve mechanism (discs and/or rings) is achieved via the sealing means. This allows for the additional introduction of instruments with large radii of curvature. The trocar tube in accordance with the invention is centered during placement and automatically seats after removal of the trocar plunger. A defined pretensioning of the trocar tube and the attachment at the trocar plunger can be prepared prior to use. An impermissible excessive stretching of the trocar tube in the axial direction does not occur. In addition to the required flexibility, the system is gas-tight along the entire length of the trocar tube as well as in the vicinity of the valve mechanism and easy cleaning and disassembly of the entire system is likewise guaranteed. Individual components, such as the sealing discs, are easily accessible and can be easily replaced.

In accordance with the invention not only sealing rings but also sealing discs can surround the trocar plunger in a gas-sealing-fashion within the valve housing. Sealing discs have the advantage of being able to automatically close the lumen in a sufficiently gas-tight manner when the trocar plunger is retracted.

Further advantages can be derived from the description and the accompanying drawing. The above mentioned features as well as those to be described below can be used in accordance with the invention individually or collectively in arbitrary combination. The embodiments mentioned are not to be considered as exhaustive enumeration, rather have exemplary character only.

The invention is represented in the drawing and explained in connection with embodiments.

BRIEF DESCRIPTION OF THE DRAWING

FIG. 1 shows a trocar system in accordance with the invention comprising a trocar tube having a valve housing and a trocar plunger;

FIG. 2 shows a trocar tube with opened valve housing which accepts the individual components shown in the figure.

DESCRIPTION OF THE PERFERRED EMBODIMENT

The figures of the drawing show the object in accordance with the invention in a partially schematic fashion and the dimensions illustrated are not to be strictly taken to scale.

FIG. 1 shows a trocar system 10 comprising a trocar tube 11, a trocar plunger 12 and a valve housing 13 connected to the trocar tube 11. A circular shoulder 15 is formed in the tip region 14 of the trocar plunger 12 to which a conical mandril 16 is adjacent. A shaft section 17 of the trocar plunger 12, which extends from the tip region 14 up to a handle 18, has a reduced diameter compared to tip region 14. The handle 18 is formed on the trocar plunger 12 opposite to the tip region 14 at which the trocar plunger 12 can be grasped and pushed through the valve housing 13 into the trocar tube 11.

A sealing cap 20, formed on the valve housing 13, is made from a rubber elastic material and can sealingly surround the trocar plunger 12 when same has been introduced into the valve housing 13 and the trocar tube shaft. The trocar tube 11 is tapered at the end 21 next to the patient.

The trocar tube 11 is manufactured from a spiral 22 surrounded by a rubber elastic plastic material. The individual spiral windings are separated from each other and the gaps between the spiral windings are likewise filled by the plastic material. The trocar tube 11 is flexible in the direction of arrow 23 and can also be stretched in the direction of arrow 24. The spiral 22 is preferentially made from a metal spiral.

In the event that a trocar plunger 12, having a length which is greater than that of the trocar tube 11 including the valve housing 13, is inserted into the trocar tube 11, it is possible to insert the trocar plunger 12 into the trocar tube 11 only up to the point where the circular step or shoulder 15 of the trocar plunger 12 lockingly engages the taper at the end 21 of the trocar tube 11 next to the patient. In the event that the trocar plunger 12 is further inserted in the direction of arrow 24 with the valve housing 13 being stationary, the trocar tube 11 stretches in the direction of arrow 24.

The valve housing 13 is constructed in a manner allowing disassembling of same and is held together by means of clamps 25. Two clamps 25 are shown in FIG. 1.

FIG. 2 shows a trocar tube 11 and a valve housing 13 opened and with disassociated individual components arranged within the valve housing 13. The trocar tube 11 can be inserted into the valve housing 13 via the taper at the end 21 next to the patient. A flange 26 is formed on the trocar tube 11 and seats on a housing floor 27 of the valve housing 13 when the trocar tube 11 is inserted. With the trocar tube 11 being inserted into the valve housing 13, a support ring 28 made from a tough elastic material or from a material having a stable shape is placed onto the flange 26 for stabilizing purposes. A sealing ring 29, at which the first sealing disc 30 and the second sealing disc 32 are supported, is placed onto the support ring 28. The sealing discs 30, 31 have slits 30', 31' to allow the trocar plunger 12 to penetrate through the valve housing 13 when the valve housing 13 is closed. The slits 30', 31' can be positioned on top of each other rotated with respect to each other by 90°. The valve housing 13 can be closed by means of a housing lid 32 which is pressed onto the inserted components within the valve housing 13 by means of clamps 25. A tubular shoulder 33 is formed on the housing lid 32 onto which the rubber elastic sealing cap 20 can be placed.

Retention means can be provided for on the outer surface of the trocar tube 11 to securely fix the position of the trocar tube 11 within the tissue. Tabs or ring-shaped flanges are suitable as retention means which open when the trocar tube 11 is retracted out of the tissue to generate an opposing force. In the event that the force exercised during retraction of the trocar tube 11 exceeds the maximum opposing force, these retention means can flip-over in the retraction direction of the trocar tube 11 to seat against the outer surface. In the event that the maximum retaining force of the retention means is exceeded, it is possible for the trocar tube 11 to be removed from the tissue without exercising additional increased force. Spirals introduced onto the outer surface of the trocar tube or an inflatable cuff are suitable as retention means. The retention means are preferentially formed below the valve housing 13 at a certain separation therefrom and along a certain axial length on the trocar tube shaft.

A trocar system 10 comprises a trocar tube 11, a trocar plunger 12 and a valve housing 13 formed at the end of the trocar tube 11 facing away from the patient. The trocar tube 11 is produced from a flexible material which is stabilized by a spiral 22. The trocar tube 11 has a taper at the end 21 next to the patient which can be supported at a circular shoulder 15 with the trocar plunger 12 inserted into the trocar tube 11. The trocar tube 11 can be bent in the direction of arrow 23 and stretched in the direction of arrow 24.

We claim:

1. A trocar system comprising:
    a trocar plunger having one of a circular step and a conical section at a tip thereof;
    a flexible trocar tube defining a lumen, said tube being stretchable along an axial length thereof, said tube having a taper at an end proximate to a patient, said taper interlocking with at least one of said circular step or conical section; and
    a valve mechanism formed at an end of said trocar tube facing away from a patient, said valve mechanism having a valve housing adapted for passage of said trocar plunger for insertion of said trocar plunger into said trocar tube.

2. The trocar system of claim 1, wherein said trocar tube comprises a spiral jacketed in elastic material.

3. The trocar system of claim 2, wherein said spiral comprises individual spiral windings and said elastic material closes intermediate spaces between said spiral windings along an axial length of said trocar tube.

4. The trocar system of claim 1, wherein said trocar plunger has an axial length greater than an axial length of said trocar tube in a non-operative state.

5. The trocar system of claim 1, wherein said valve mechanism is held within said valve housing, said valve housing comprising an elastic seal surrounding said trocar plunger within said trocar tube in a gas-tight fashion, said elastic seal closing said lumen in a gas-tight fashion when said trocar plunger is removed.

6. The trocar system of claim 1, wherein said valve housing is adapted for disassembly thereof.

7. The trocar system of claim 1, wherein said trocar plunger, said trocar tube, and said value mechanism are manufactured from material which can be cleaned and sterilized.

8. The trocar system of claim 1, wherein said trocar tube comprises retention means on an outer peripheral surface.

9. The trocar system of claim 8, wherein said retention means are located at an end facing away from a patient.

10. The trocar system of claim 8, wherein said retention means comprise at least one of tabs, wings, wing-shaped elements and an inflatable cuff.

* * * * *